(12) United States Patent
Lanfranchi et al.

(10) Patent No.: US 6,527,551 B2
(45) Date of Patent: Mar. 4, 2003

(54) DENTAL IRRIGATION DEVICE

(76) Inventors: Alfred Lanfranchi, 17 Mitchell Ct., Marlboro, NJ (US) 07746; James Cavallaro, 1455 70th St., Brooklyn, NY (US) 11228

( * ) Notice: Subject to any disclaimer, the term of this patent is extended or adjusted under 35 U.S.C. 154(b) by 0 days.

(21) Appl. No.: 09/947,813

(22) Filed: Sep. 6, 2001

(65) Prior Publication Data

US 2002/0028420 A1 Mar. 7, 2002

Related U.S. Application Data

(60) Provisional application No. 60/230,269, filed on Sep. 6, 2000.

(51) Int. Cl.[7] .......................... A61C 15/00; A61C 17/02
(52) U.S. Cl. ........................................ 433/77; 433/80
(58) Field of Search ........................ 433/77, 80, 88, 433/97, 79, 78; 601/161, 162

(56) References Cited

U.S. PATENT DOCUMENTS

| | | | |
|---|---|---|---|
| 4,442,830 A | 4/1984 | Markau | 433/80 |
| 4,585,415 A | 4/1986 | Hommann | 433/80 |
| 4,958,963 A * | 9/1990 | Perrault | 433/79 |
| 4,979,504 A | 12/1990 | Mills | 604/73 |
| 5,033,961 A | 7/1991 | Kandler et al. | 433/89 |
| 5,055,043 A | 10/1991 | Weiss et al. | 433/86 |
| 5,087,198 A | 2/1992 | Castellini | 433/80 |
| 5,218,956 A | 6/1993 | Handler et al. | 604/19 |
| 5,220,914 A | 6/1993 | Thompson | |
| 5,257,933 A | 11/1993 | Jousson | 433/80 |
| 5,277,582 A | 1/1994 | Jousson | 433/80 |
| 5,503,553 A | 4/1996 | Hines | 433/80 |
| 5,626,472 A | 5/1997 | Pennetta | 433/80 |
| 5,934,902 A | 8/1999 | Abahusayn | 433/80 |
| 5,961,327 A | 10/1999 | Löhn | 433/80 |

* cited by examiner

*Primary Examiner*—Cary E. O'Connor
(74) *Attorney, Agent, or Firm*—Dilworth & Barrese, LLP

(57) ABSTRACT

A dental irrigation device is provided having an irrigation system and a pressurizer. The irrigation system includes a reservoir having a volume of at least approximately eight ounces and an attachment mechanism adapted for positioning the reservoir on a bar of a dental unit. The reservoir has a connector configured for providing an irrigant under pressure to a handpiece adapted for use with dental tools by a surgeon. The irrigant may be pressurized by an external source of compressed air through the connector, for example, or have a pump in communication with the irrigant.

17 Claims, 3 Drawing Sheets

DENTAL IRRIGATION DEVICE

CROSS REFERENCE TO RELATED APPLICATIONS

This application claims priority from applicants' provisional application No. 60/230,269, filed Sep. 6, 2000.

BACKGROUND

1. Technical Field

The present disclosure relates to dental irrigation devices and methods of irrigating dental tissue, and more particularly, to devices and methods for providing a continuous and controlled flow of a dental irrigation fluid for patient treatment.

2. Description of Related Art

The most common apparatuses for dental irrigation are conventionally employed irrigation triple syringes which require a dentist and a dental assistant to pass back and forth new and exhausted triple syringes. More complex systems have been developed for providing an irrigant for dental treatment including U.S. Pat No. 5,055,043 to Weiss et al. and U.S. Pat. No. 5,087,198 to Castellini.

Weiss et al. teaches a permanent and complex system of fluid lines and valves interconnected with external sources of compressed air, oxygen, treatment solution, and water for the transferring, mixing, and dispensing of medicaments. Similarly, Castellini teaches the directing of air and water to a plurality of permanently connected instruments. The system further including a reservoir containing a supply of a medical solution and a fluid line connecting the reservoir to a water supply circuit. The Castellini apparatus further teaches a three-way directional control valve for the variable control of the independent sources of water and medical solution.

The present dental irrigation apparatuses such as Weiss et al. and Castellini are complex systems that are cumbersome, complex to use, and require permanent installations.

Accordingly, a need exists for an improved and simplified device for dental irrigation that can provide an instantaneous flow of an irrigant in conjunction with conventional flow control devices that may be readily adapted for use with a dental unit, requiring only a minimal amount of external support. In addition, a further need exists for a dental irrigation device configured at least partially as a disposable device that may be used in a single application or for a controlled period of time.

SUMMARY

A dental irrigation device including an irrigation system and means for pressurization. The irrigation system includes a reservoir and an attachment mechanism adapted for positioning the reservoir on a bar of a dental unit. The reservoir is also configured with connecting means for providing an irrigant under pressure through a flexible tube to a handpiece adapted for use with dental tools by a surgeon. The reservoir of irrigant may be pressurized through connecting means by an external source of compressed air, for example, or by a pump in direct communication with the irrigant.

A method is provided for the treating a patient with the dental irrigation device including attaching the reservoir to the dental unit using an attachment mechanism and using connecting means to connecting the reservoir to a handpiece adapted for use with dental tools. Pressurizing the irrigant using pressurization means to deliver the irrigant under pressure to the dental tools.

It is to be understood that both the foregoing general description and the following detailed description are exemplary and explanatory and are presented to provide further information on the invention as claimed.

BRIEF DESCRIPTION OF THE DRAWINGS

Various embodiments are described herein with reference to the drawings, wherein.

DETAILED DESCRIPTION

Figure 1:
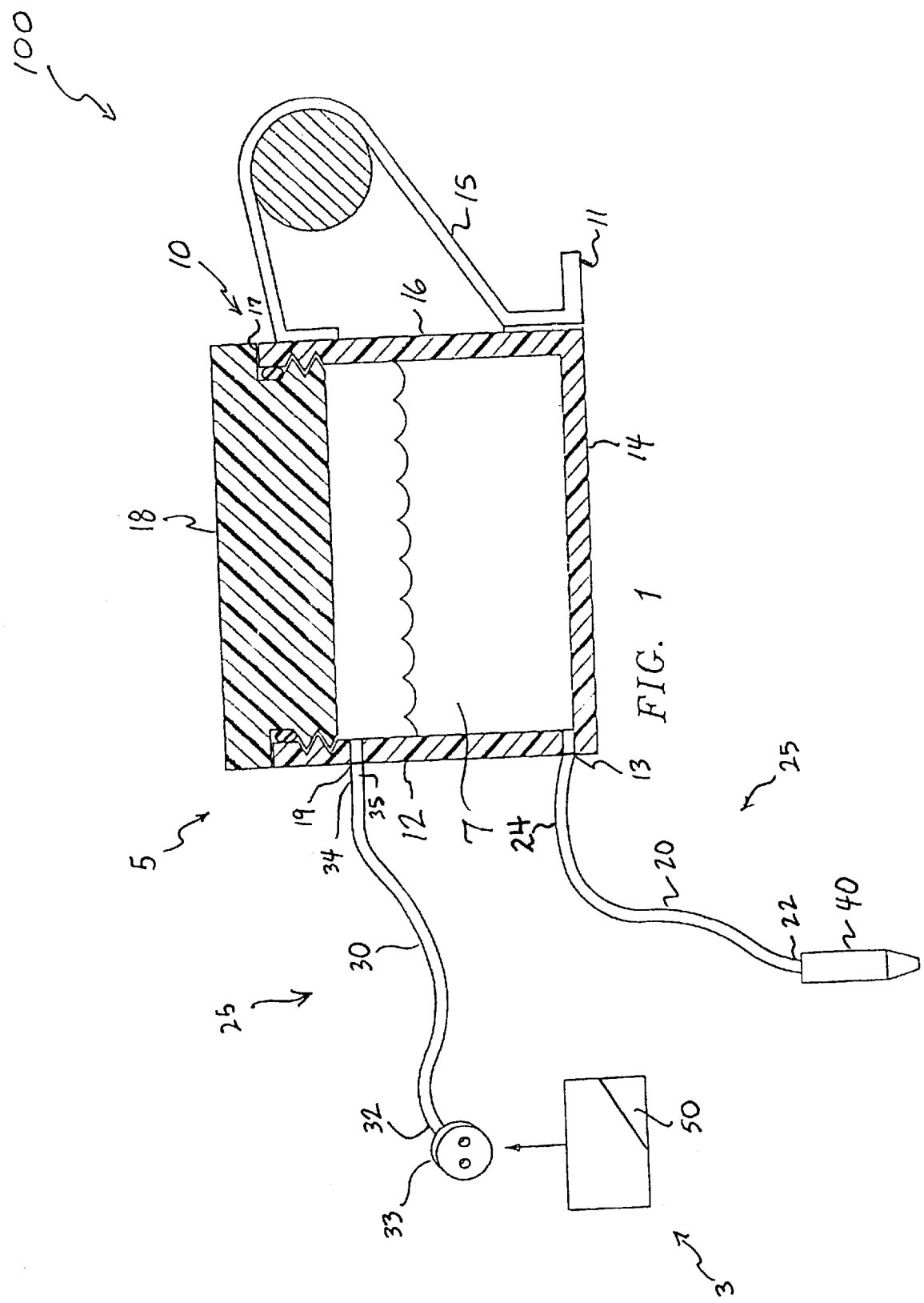
FIG. 1 is a plan view of one embodiment of the dental irrigation device constructed in accordance with the present disclosure.
Figure 3:
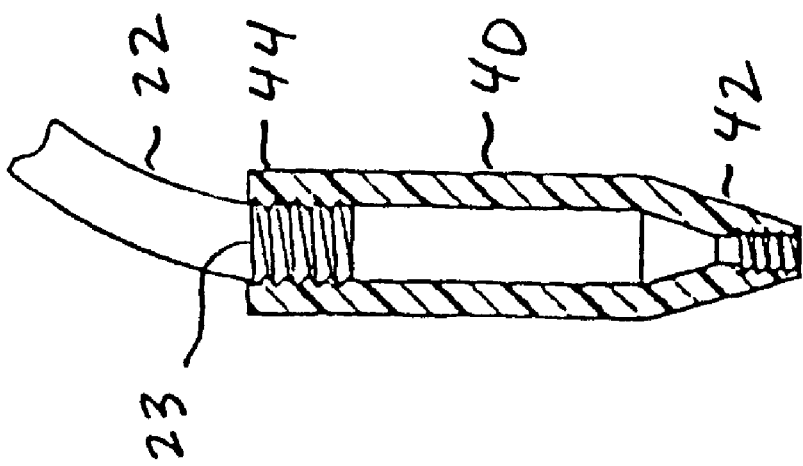
FIG. 3 is a cross sectional view of a handpiece of the dental irrigation device of FIG. 1.
Figure 2:
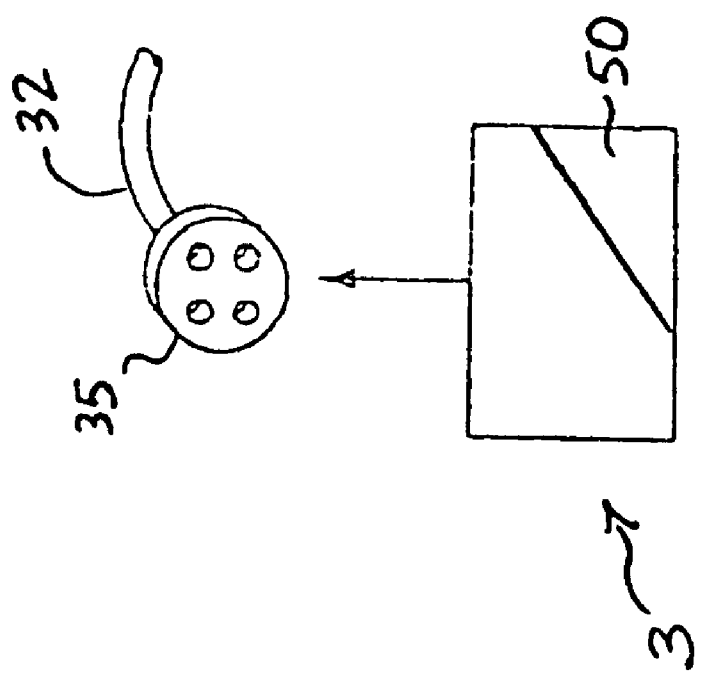
FIG. 2 is a detail of FIG. 1 showing a perspective view of an alternative connector configuration interfacing between a flexible tube and a conventional dental unit providing means for pressurization.

Referring now to FIGS. 1–3, a dental irrigation device 100 is configured to provide a source of irrigant 7 mountable directly to the front of the dental delivery system that requires minimal support from external sources, is readily adaptable to current dental treatment systems, and is suitable for use with at least one patient. The dental irrigation device 100 or portions of thereof may also be advantageously configured for sterilization and reuse or disposal after a single use.

Dental irrigation device 100 includes an irrigation system 5 for providing an irrigant 7, a liquid such as isotonic saline, water, or medicants, under pressure to standard dental tools for the treatment of dental patients. Connecting means 25 is adapted for use with an integral pressurization means 3 and a source of power 50 or with pressurization means 3 and a source of power 50 separate from dental irrigation device 100.

Irrigation system 5 includes a reservoir 10, an attachment mechanism 15, connecting means 25, and a handpiece 40 configured for use with standard dental tools or instruments.

Reservoir 10 preferably has the structural shape of a jar or container 12 having a bottom 14, and sides 16 defining an edge 17. Container 12 defines an internal cavity configured for a receiving at least approximately eight ounces of irrigant 7. In the vicinity of edge 17 is a screw type threaded interface for a cap 18. In the alternative, reservoir 10 may be a sealed container provided as an assembly containing irrigant with or without tubing. Reservoir 10 is preferably made of a medical grade plastic, but other medical grade materials are also envisaged such as e.g. stainless steel, titanium, different plastics, rubber, or composite materials, etc.

Attachment mechanism 15 includes at least one device, such as a hook and loop strap, positioned on side 16 configured for attaching reservoir 10 to a portion of a bar on a dental unit in an upright position. The hook strap, in one preferred embodiment, runs from the vicinity of the edge 17 to the vicinity of bottom 14 on side 16 of reservoir 10. The bar of the dental unit is positioned in juxtaposition with side 16 or separated from side 16 by a hook and look strap having a rigid portion and may further include enhancements for increasing its frictional bond with the dental unit, such as a clamping, clipping, or locking mechanism. Attachment mechanism 15 also includes a cantilevered portion 11 that may assist in the retention of the hook and loop on the dental bar by the use of the clipping type mechanism, for example. Attachment mechanism 15 is configured for the ease of removal and replacement of reservoir 10 from the dental bar.

Connecting means 25, such as an external connector 13 of reservoir 10 and a tube 20, is configured for communicating irrigant 7 to handpiece 40. Connector 13 can be configured as a simple open connection or a valve assembly capable of opening and closing the connector. Tube 20 is preferably a standard size flexible tubular hose having an inside diameter of approximately one quarter inch. Tube 20 has a first end 22 configured with a connector 23 for interfacing with a handpiece 40. Second end 24 has a connector 25 is configured to couple with connector 13. Reservoir 10 can be configured with tube 20 being permanently attached or as a separate element that requires assembly.

Handpiece 40 has a distal end 42 and a proximal end 44. Distal end 42 includes a standard dental handpiece interface utilizing internal threads configured to be adapted for use with dental tools dispensing irrigant 7 such as syringe irrigation tips, for example. Depending upon the application, handpiece 40 or the tool installed on the distal end may have a pedal operated rheostat for the dentist to control the flow of irrigant 7 to the requirements of a given procedure. Proximal end 44 includes internal threads configured for coupling with connector 23 of tube 20. Handpiece 40 and tube 20 can include safety related devices known in the art such as one way valves to preclude contamination, etc.

Connecting means 25 is adapted for use with pressurization means 3. Pressurization means 3 includes a source of power 50 which can be configured as being integral with irrigation system 5 or as an external, separate pressurization means 3 and source of power 50, or variations thereof coupled to irrigation system 5 through connecting means 25. Source of power 50 may also directly provide energy for the means for pressurization 3 of irrigant 7 in irrigation system 5 or be a provider of energy operatively connected through connecting means 25 with pressurization means 3.

In one preferred embodiment, source of power 50 is a standard external source of air pressure providing pressurization means 3 to irrigation system 5 through connecting means 25 such as a second flexible tubular hose or tube 30 and a second connector 19. Second connector 19 is positioned on reservoir 10, to include cap 18, above the level of irrigant. Second connector 19 is configured for being coupled with a connector 35 positioned on a proximal end 34 of second flexible tube 30 and an opposing end 32 having a connector 33 is configured to interface with standard connection systems such as a two hole 33 or a four hole 35 airline hose, for example. The external source of power providing the means through the second tube 30 and second connector 19 to suitably pressurize irrigant 7 for distribution through irrigation system 5.

Figure 4:
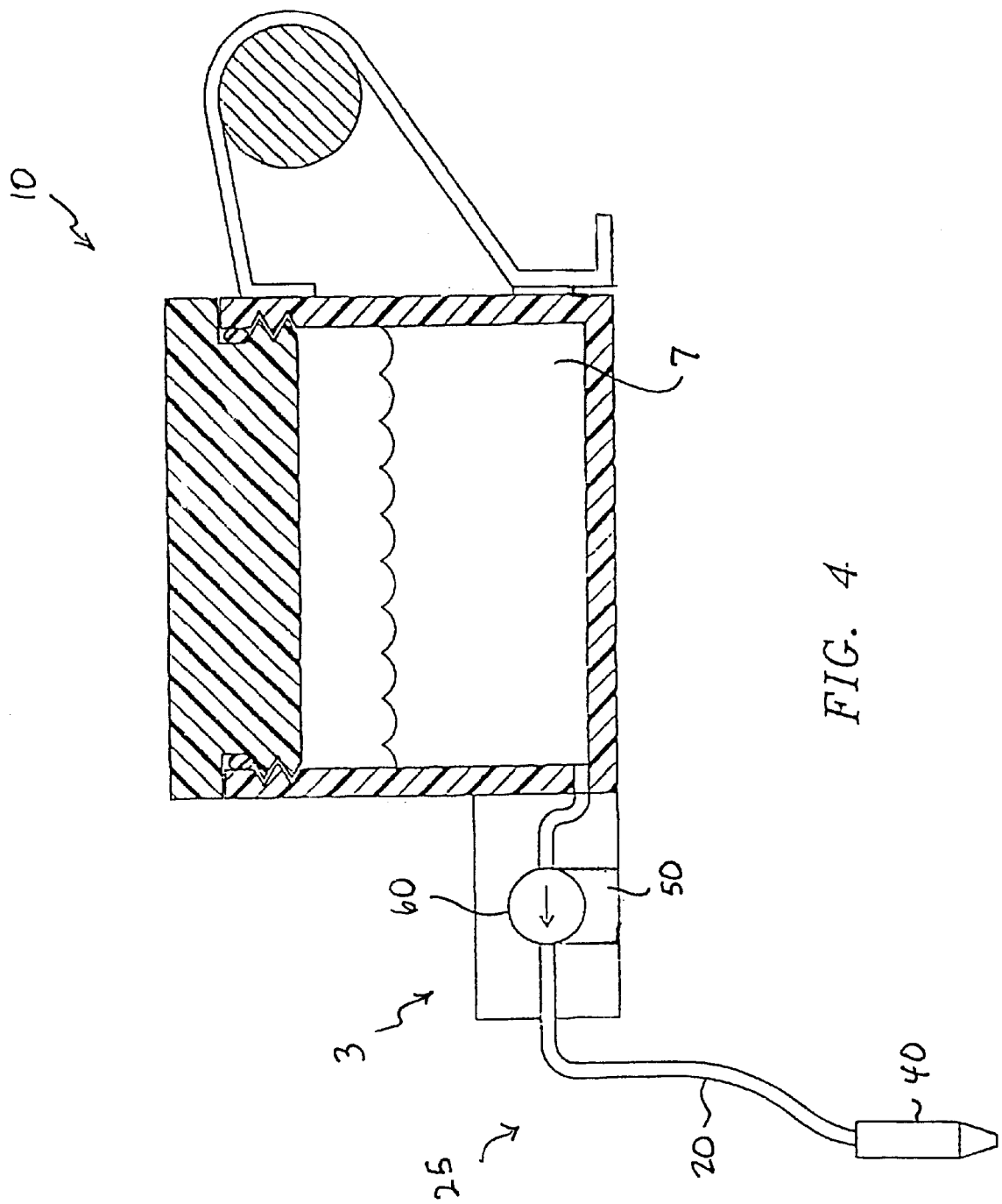
FIG. 4 is a plan view of a second embodiment of the dental irrigation device having pressurization means integral with the reservoir constructed in accordance with the present disclosure.

Referring now to FIG. 4, a second preferred embodiment is shown wherein pressurization means 3 includes a pump 60 having a source of power 50 which can be integrally positioned with pump 60 or positioned separately as an external source. Pump 60 can be positioned directly on or submerged within reservoir 10, but is in communication with and provides pressurization to irrigant 7, using connecting means 25 for distribution to handpiece 40, such as connector 13 and tube 20. Pump 60 can be configured as a small battery operated electrical pump having a rechargeable battery, for example, or an electrical pump coupled to an external source of electrical power 50, or a pump operated by compressed air. These alternative sources of power 50 and means of pressurization 3 could also accommodate variable flow control devices operable by remote means such as a foot pedal or handswitch, for example.

Referring now to FIGS. 1–4, in operation irrigation system 5 including reservoir 10, containing at least approximately eight ounces of irrigant, is positioned on a bar of a dental unit. Tube 20 is connected to handpiece 40 and to connector 13. Handpiece 40 is adapted for use with standard dental tools having a foot actuated rheostat to control the flow of irrigant 7. Second tube 30 is connected with a source of air pressure and a second connector 19. Reservoir 10 is then opened, filled with irrigant, and sealed. The source of power 50 is then actuated providing a means of pressurization of irrigant 7. The dental tool is then turned on to apply irrigant 7 to a patient.

Alternatively, irrigation system 5 includes reservoir 10 having an integrated means of pressurization 3 connected with an external source of power 50. Source of power 50 can be configured to provide pneumatic or electrical power as suitable for a given pump providing means of pressurization 3 for irrigation system 5.

In a further alternative, irrigation system 5 includes reservoir 10 having an integral battery powered source of power 50 providing means of pressurization 3. Connecting means 25, such as tube 20 is connected to the means of pressurization 3 positioned to be in fluid communication with reservoir 10 and to handpiece 40. Reservoir 10 is then opened, filled with irrigant, and sealed. The source of power 50 is then actuated providing means of pressurization 3 to irrigant 7. The dental tool is then turned on to apply irrigant 7 to a patient.

Upon completion of the application of irrigant for a first patient, the dentist may change tools and apply the remaining portion of irrigant to a second patient. In the alternative, the dentist can refill reservoir 10 on the dental unit or remove reservoir 10, refill reservoir 10, and reposition reservoir 10 on the dental unit. Refilling reservoir 10 includes unscrewing cap 18, pouring irrigant into container 12, and screwing cap 18 sufficiently closed to ensure an air tight seal with container 12.

In the alternative, when the supply of irrigant is exhausted or at the election of the dentist, one or more components of irrigation system 5 such as reservoir 10 and tubes 20 and 30 may be readily disconnected and discarded and a new reservoir 10, tube 20, and tube 30, and handpiece 40 positioned in the dental unit.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. An independent dental irrigation device comprising:
 a reservoir including a container and an attachment mechanism, the reservoir being configured for holding an irrigant, the attachment mechanism having hook and loop type straps connected to the container and adapted for use with a bar of a dental unit;
 a handpiece having a proximal end and a distal end, the handpiece being adapted for use with standard dental tools configured for dental irrigation; and connecting means connecting the irrigant positioned in the reservoir to the handpiece and being adapted for use with means for pressurization of the irrigant.

2. The dental irrigation device of claim 1, wherein the reservoir has a configuration suitable for holding at least approximately eight ounces of irrigant and connecting means including a first connector arid a second connector, the first connector being positioned in fluid communication with the irrigant and the handpiece, the second connector positioned above the level of the irrigant in the reservoir, the second connector being in communication with means of pressurization.

3. The dental irrigation device of claim 2, wherein the connecting means includes at least one tube, wherein a first tube is in fluid communication with the first connector and the handpiece and a second tube is in fluid communication with the second connector and means for pressurization.

4. The dental irrigation device of claim 3, wherein the connecting means is adapted for use with the means of pressurization, the means for pressurization being an external source of air pressure in communication with the irrigant, the source of air pressure being suitable for providing pressure to the irrigant in the handpiece.

5. The dental irrigation device of claim 1, wherein the means for pressurization is integrated with the connecting means and the reservoir, the means for pressurization providing suitably pressurized irrigant to the handpiece.

6. The dental irrigation device of claim 1, wherein the means for pressurization is a pump connected with a source of power and the pump is in fluid communication with connecting means.

7. The dental irrigation device of claim 1, wherein at least the reservoir is configured for sterilization by an autoclave.

8. A method for using a dental irrigation device comprising:

providing an irrigation system including a reservoir, a handpiece, means for pressurization and connecting means including at least one tube, the reservoir including an attachment mechanism having a hook and a loop device, which are adapted for use on a bar of a dental unit, the handpiece being adapted for use with tools configured for dental irrigation, the at least one tube being configured for communicating fluid to the handpiece;

positioning the reservoir on the bar of the dental unit by using the hook and the loop device, the reservoir containing an irrigant;

applying means for pressurization to the irrigant; and treating at least one patient with the irrigant.

9. The method for using a dental irrigation device of claim 8, wherein step of applying includes using connecting means to connect the irrigant with means for pressurization.

10. The method for using a dental irrigation device of claim 8, wherein the treating of the patient includes disposing of the reservoir and tubes removed from the dental unit and positioning a new reservoir adapted for use with the bar of a dental unit and connecting the new tubes.

11. The method for using a dental irrigation device of claim 8, wherein step of treating at least one patient includes removing at least the reservoir, cleaning the reservoir, and autoclaving at least the reservoir.

12. The method for using a dental irrigation device of claim 8, wherein step of positioning includes filling the reservoir with an irrigant prior to positioning on the dental unit.

13. The method for using a dental irrigation device of claim 8, wherein step of positioning includes positioning a reservoir having an irrigant sealed therein and releasing the irrigant to at least one tube.

14. A method for using a dental irrigation device comprising:

providing an irrigation system including a reservoir having an attachment mechanism, connecting means including a first tube and a second tube, a handpiece, and means for pressurization;

using an attachment mechanism adapted for use on a dental unit to position the reservoir on a bar of the dental unit;

connecting the first tube to a first connector of the reservoir and the handpiece, the handpiece being adapted for use with dental tools;

connecting the second tube to a second connector of the reservoir and means for pressurization;

applying means for pressurization of the irrigant; and treating at least one patient with the irrigant including removing the reservoir when it is exhausted and refilling the reservoir and repositioning the reservoir on the bar of the dental unit.

15. The method for using a dental irrigation device of claim 14, wherein the positioning of the reservoir includes using a hook and loop adapted for use with the bar of the dental unit.

16. The method for using a dental irrigation device of claim 14, wherein the positioning of the reservoir includes filling the reservoir with an irrigant.

17. The method of using a dental irrigation device of claim 14, wherein the step of treating the patient includes removing the reservoir when it is exhausted and autoclaving the reservoir, tubes, and handpiece and repositioning the irrigation system for treatment.

\* \* \* \* \*